US012595219B2

(12) United States Patent
Palmieri et al.

(10) Patent No.: US 12,595,219 B2
(45) Date of Patent: Apr. 7, 2026

(54) CONTINUOS FLOW SYNTHESIS OF CANNABIDIOL

(71) Applicant: Indena S.P.A., Milan (IT)

(72) Inventors: Alessandro Palmieri, Camerino (IT); Roberto Ballini, Camerino (IT); Pietro Allegrini, Milan (IT); Daniele Ciceri, Milan (IT)

(73) Assignee: Indena S.P.A., Milan (IT)

( * ) Notice: Subject to any disclaimer, the term of this patent is extended or adjusted under 35 U.S.C. 154(b) by 17 days.

(21) Appl. No.: 17/293,745

(22) PCT Filed: Nov. 11, 2019

(86) PCT No.: PCT/EP2019/080780
§ 371 (c)(1),
(2) Date: May 13, 2021

(87) PCT Pub. No.: WO2020/099283
PCT Pub. Date: May 22, 2020

(65) Prior Publication Data
US 2022/0009865 A1 Jan. 13, 2022

(30) Foreign Application Priority Data
Nov. 14, 2018 (EP) .................................... 18206248

(51) Int. Cl.
*C07C 37/16* (2006.01)
*C07C 37/14* (2006.01)
*C07C 37/72* (2006.01)
*C07C 37/82* (2006.01)

(52) U.S. Cl.
CPC .............. *C07C 37/16* (2013.01); *C07C 37/14* (2013.01); *C07C 37/72* (2013.01); *C07C 37/82* (2013.01); *C07C 2601/16* (2017.05)

(58) Field of Classification Search
CPC ......... C07C 37/14; C07C 37/72; C07C 37/82; C07C 2601/16
See application file for complete search history.

(56) References Cited

U.S. PATENT DOCUMENTS 2,894,040 A * 7/1959 Bain ....................... C07C 33/14
568/825
2008/0108122 A1* 5/2008 Paul .................... B01F 33/3012
422/129
2015/0336874 A1 11/2015 Koch et al.

FOREIGN PATENT DOCUMENTS

JP 2008101000 A 5/2008
JP 2016531919 A 10/2016

OTHER PUBLICATIONS

Baek et al. ("Boron Trifluoride Etherate on Alumina—A Modified Lewis Acid Reagent. An Improved Synthesis of Cannabidiol", Tetrahedron Letters, 1985, vol. 26, No. 8, pp. 1083-1086) (Year: 1985).*
Cardillo et al. (Gazzetta Chimica Italiana, 1973, vol. 103., pp. 127-139). (Year: 1973).*
Razdan et al. ("Hashish. A Simple One-Step Synthesis of (-)-Δ1-Tetrahydrocannabinol (THC) from p-Mentha-2,8-dien-1-ol and Olivetol", Journal of the American Chemical Society, Sep. 1974, vol. 96, No. 18, pp. 5860-5865). (Year: 1974).*
Vogel's Textbook of Practical Organic Chemistry, fifth edition, 1989, p. 33. (Year: 1989).*

(Continued)

*Primary Examiner* — Sikarl A Witherspoon
(74) *Attorney, Agent, or Firm* — Silvia Salvadori, P.C.; Silvia Salvadori

(57) ABSTRACT

A process for the synthesis of Cannabidiol of formula (1): (1) is herein disclosed. The process comprises contacting a solution [solution (S1)] of (+)-p-mentha-diene-3-ol of formula (4) (4) or an ester thereof and olivetol of formula (3): (3) with a solution [solution (S2)] of a non-supported Lewis acid in a continuous flow reactor and treatment of the resulting mixture with a basic solution. The process offers the advantage that it can be conveniently carried out on an industrial scale while avoiding the formation of abnormal CBD and THC (Δ9-tetrahydrocannabinol).

(1)

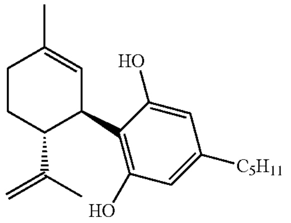

(4)

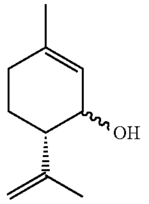

(3)

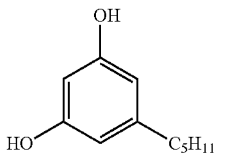

12 Claims, No Drawings

(56) References Cited

OTHER PUBLICATIONS

Lumir O., et al., "Enantiomeric cannabidiol derivatives: synthesis and binding to cannabinoid receptors", Organic & Biomolecular Chemistry, vol. 3, No. 6, Jan. 1, 2005, p. 1116-1123.

Search Report and Written Opinion of PCT/EP2019/080780 of Mar. 9, 2020.

Cardillo B et al. "Alkylation of resorcinols with monoterpenoid allylic alcohols in aqueous acid: synthesis of new cannabinoid derivatives", Gazzetta Chimica Italiana, 103, 1973 pp. 127-139.

Office Action issued Oct. 18, 2023 in counterpart Japanese Patent Application No. 2021-525742.

* cited by examiner

CONTINUOS FLOW SYNTHESIS OF CANNABIDIOL

This application is a U.S. national stage of PCT/EP2019/080780 filed on 11 Nov. 2019, which claims priority to and the benefit of European Application No. 18206248.9 filed on 14 Nov. 2018, the contents of which are incorporated herein by reference in their entireties.

FIELD OF THE INVENTION

The present invention relates to a process for the synthesis of Cannabidiol.

BACKGROUND OF THE INVENTION

Cannabidiol (CBD), of formula (1), the major non-psycotropic phytocannabinoid in most cannabis preparations, has been found to have antiepileptic, anti-anxiety and anti-dystonia properties in man.

(1)

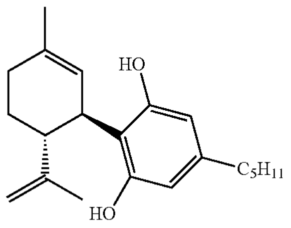

*Cannabis sativa* is currently the most used source of CBD, but the prospect of rapid growth of CBD demand makes the direct synthesis of CBD desirable. The most efficient routes to CBD synthesis are the condensation between (+)-p-mentha-diene-1-ol of formula (2):

(2)

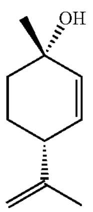

with olivetol of formula (3)

(3)

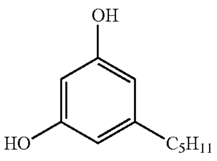

and the condensation of (+)-p-mentha-diene-3-ol of formula (4):

(4)

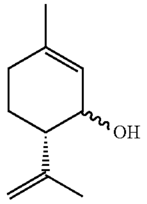

with olivetol (3)

in the presence of acids such as trifluoroacetic acid, p-toluenesulfonic acid, hydrochloric acid, $BF_3$-etherate ($BF_3$-$Et_2O$) or weak acids, as disclosed in Lago-Fernandez et al. Methods in enzymology, Vol. 593, 237-257 (2017).

Such approaches lead to the formation of considerable amounts of two undesired products, the unnatural CBD isomer (abnormal-CBD) of formula (5):

(5)

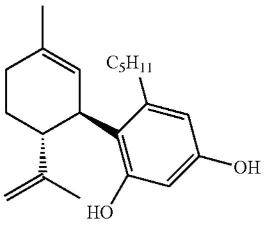

Abnormal-CBD and the psychotropic phytocannabinoid $\Delta^9$-tetrahydrocannabinol (THC) of formula (6)

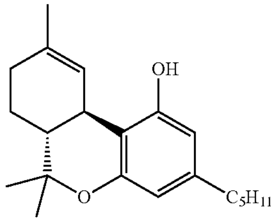

THC

The formation of amounts of THC above legal limits, which vary from country to country and the fact that THC has been associated with acute psychosis, make CBD production by chemical synthesis complicated from the regulatory standpoint.

Moreover, due to lack of selectivity, the available synthetic routes provide yields of CBD that are too low for industrial application. As a mere title of example, Petrzilka et al. [Helvetica Chimica Acta, 52, 4, (1969), 123, 1102] reported yields of CBD around 20%.

The problem of THC formation had been already investigated by Baek, S. et al. (Tetrahedron Letters, Vol. 26, No. 8, pp 1083-1086, 1985), who discovered that reacting (+)-p-mentha-diene-1-ol (2) with olivetol (3) in the presence of $BF_3$-$Et_2O$ supported on alumina or silica could reduce the formation of THC and, at the same time, improve the CBD yield up to a molar yield of 55%. When the same conditions were applied to (+)-p-mentha-diene-3-ol (2) and olivetol (3) (Lumir et al., Org. Biomol. Chem., 2005, 3, 1116-1123), the yield of CBD dropped to 44%, but still with no formation of THC. In 1993, Baek S. et al. (Bull. Korean Chem. Soc., Vol. 14, No. 2, 1993) found it suitable to use $BF_3$-$Et_2O$ supported on alumina for the preparation of Olivetols, reporting that, in the absence of alumina the reactions yields were lower due to cyclization reactions. On the other hand, the use of $BF_3$-$Et_2O$ supported on alumina, which is not commercially available, impairs the process for the production of CBD for several reasons: 1) it needs to be prepared in situ before the reaction, 2) the environmental E-factor (total waste/product ratio) is increased due to the use of a ten-fold excess of alumina compared to the actual catalyst ($BF_3$-$Et_2O$) and 3) it cannot be recycled.

Therefore, the need is still felt for a method for the synthesis of CBD that allows to overcome the above drawbacks and, at the same time, allows to reduce the formation of THC.

On the other hand, the use of continuous flow reactors, in particular micro-reactors, in the chemical industry has greatly increased in recently years, thanks to their high heat transfer capacity, high mixing rates and their operating flexibility.

DESCRIPTION OF THE INVENTION

The Applicant has surprisingly found out that, when the reaction between (+)-p-mentha-diene-3-ol (4) with olivetol (3) is carried out in a continuous flow reactor in the presence of a non-supported Lewis acid as catalyst, CBD is obtained with molar 34% yield and no formation of THC. Even more surprisingly, when esters of (+)-p-mentha-diene-3-ol (4), in particular the acetyl ester of formula (7) [(+)-p-mentha-diene-3-ol acetate]:

(7)

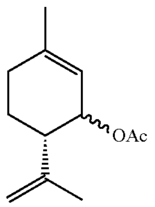

and olivetol (3) are reacted with a non-supported Lewis acid in a continuous flow reactor, a yield of 51% is obtained.

Accordingly, the present invention relates to a process for the synthesis of CBD, which comprises the following steps:

a) contacting a solution of (+)-p-mentha-diene-3-ol (4) or an ester thereof and olivetol (3) [solution (S1)] and a solution of a non-supported Lewis acid [solution (S2)] in a continuous flow reactor to obtain a first mixture [mixture (M1)] comprising CBD; and b) contacting mixture (M1) with a basic solution [solution (S3)] to obtain a second mixture [mixture (M2)];

c) separating CBD from mixture (M2).

For the purpose of the present invention:

the expression "continuous flow reactor" refers to an elongated tube for carrying a reagent stream, said tube having a cross-sectional dimension sufficiently small to allow for highly efficient heat transfer with its surroundings and sufficient length to achieve a desired residence time for a reagent stream. Typically, the cross sectional dimension of the tube ranges between 0.2 mm and 1 cm, while the length ranges between 10 cm to 30,000 cm. Suitable micro-reactors for carrying out the process of the invention are manufactured by Sigma Aldrich. The expression "reagent stream" refers to a mixture of reagents, solutions, and reaction components including reactants and products that flows through a reactor's tube;

unless indicated otherwise, general terms and expressions include all and each preferred terms and expressions indicated in the description as referring back or falling within those general terms and expressions;

a Lewis acid is a compound or ionic species having an empty orbital which can accept an electron pair from a donor compound; a suitable Lewis acid for carrying out the invention is $BF_3$; more preferably, $BF_3$ is used in the form of $BF_3$-$Et_2O$;

the expression "non-supported Lewis acid" means that the Lewis acid is not affixed to any other solid support, like silica and alumina, aimed at maximizing the catalyst's surface area when ranges are indicated, range ends are included.

In step a) of the process of the invention, solution (S1) and solution (S2) are pumped simultaneously by a first and a second pump of the reactor through a connector to a coil, in which they react and form mixture (M1).

Solution (S1) is comprised of (+)-p-mentha-diene-3-ol (4) or an ester thereof, preferably an ester with a straight or branched carboxylic acid having from 1 to 5 carbon atoms, more preferably the ester with acetic acid (acetic ester) (7) and olivetol (3), in a 1:1 to 1:2 molar ratio, preferably a 1:1 molar ratio, and an organic solvent, selected among $C_1$-$C_3$ chlorinated solvents, preferably dichloromethane, ethereal solvent preferably methyl tert butyl ether, alkyl esters preferably ethyl acetate, wherein each the concentration of each solute ranges between 0.5 M and 0.01 M, and is preferably 0.05 M, while solution (S2) is comprised of a Lewis acid, preferably $BF_3$, more preferably $BF_3$-etherate, and an organic solvent, which can be the same as or different from the solvent comprised in solution (S1). Preferably, solutions (S1) and (S2) comprise the same solvent, which is preferably dichloromethane. The concentration of the Lewis acid in solution (S2) ranges from 0.05 M to 0.001 M and is preferably 0.005 M. Solutions (S1) and (S2) are each pumped at a flow rate ranging from 0.1 to 1 mL/min, preferably 0.9 to 1.1 mL/min, more preferably 1 mL/min.

The reaction temperature varies from −20° C. to 40° C. and is preferably 20° C.

When (+)-p-mentha-diene-3-ol (4) is used, the residence time of mixture (M1) in the micro-reactor varies from 1 minutes to 15 minutes and is preferably 8 minutes. When an ester of (4) is used, in particular when (+)-p-mentha-diene-3-ol acetate (7) is used, the residence time of mixture (M1) in the microreactor varies from 1 minutes to 10 minutes and is preferably 7 minutes.

In step b), the contact between mixture (M1) and solution (S3) can be accomplished by quenching mixture (M1) streaming out of the reactor outlet in solution (S3) contained in a vessel. Alternatively, mixture (M1) can be conveyed to another continuous flow reactor along with solution (S3). Solution (S3) is typically an alkali metal bicarbonate aqueous solution or an alkali metal carbonate aqueous solution, preferably a sodium or potassium bicarbonate aqueous solution, more preferably a sodium bicarbonate aqueous solution. The concentration of alkali metal bicarbonate or carbonate in solution (S3) typically ranges from 1 to 30% w/w preferably, solution (S3) is saturated in the alkali metal bicarbonate salt. "Saturated" means containing the maximum amount of bicarbonate or carbonate at room pressure and temperature.

Step c) can be carried out according to methods known in the art. Typically, isolation is achieved by column chromatography.

The invention is illustrated in greater detail in the following experimental section.

Experimental Section

Materials (+)-p-mentha-diene-3-ol (4) was obtained according to R. Marin Barrios et al. Tetrahedron 2012, 68, 1105-1108.

Olivetol (3) was obtained from Sigma Aldrich.

(+)-p-mentha-diene-3-ol acetate (7) was obtained according to Prasav and Dav, Tetrahedron 1976, 32, 1437-1441.

Dichloromethane and sodium bicarbonate were obtained from Sigma Aldrich.

Methods

All exemplary synthesis reported below were carried out using a Bohlender™ PTFE tube (I.D. 0.8 mm, 16.91 m) purchased from Sigma Aldrich.

The analysis of CBD was carried out by gas chromatography (GC) according to Gambaro et al. Analytica Chimica Acta 468 (2002) 245-254.

SYNTHESIS EXAMPLES

Example 1—Synthesis of CBD from (+)-p-mentha-diene-3-ol (4) and Olivetol (3)

A solution (S1) of 0.05 M of (+)-p-mentha-diene-3-ol (4) and 0.05 M of Olivetol (3) in dichloromethane (10 mL) and a solution (S2) of $BF_3$-etherate 0.005 M (10 mol %) in dichloromethane (10 mL) were simultaneously pumped with a flow rate of 0.5 mL/min for each pump into a T-connector before passing through a 8.5 mL reactor coil maintained at 20° C. The outflow was directly quenched with a saturated aqueous solution of sodium bicarbonate (100 mL). No traces of THC were detected and CBD was isolated by column chromatography with a recovery yield of 34% mol.

Example 2—Synthesis of CBD from (+)-p-mentha-diene-3-ol Acetate (7) and Olivetol (3)

A solution of 0.05 M of (+)-p-mentha-diene-3-ol acetate (7) and 0.1 M of Olivetol (3) in dichloromethane (10 mL) and a solution of $BF_3$-etherate 0.005 M (10 mol %) in dichloromethane (10 mL) were simultaneously pumped with a flow rate of 0.5 mL/min for each pump into a T-connector before passing through a 8.5 mL reactor coil maintained at 20° C. The outflow was directly quenched with a saturated aqueous solution of sodium bicarbonate (100 mL). No traces of THC were detected and CBD was isolated with a recovery yield of 51% mol.

The invention claimed is:

1. A process for the synthesis of Cannabidiol of formula (1):

(1)

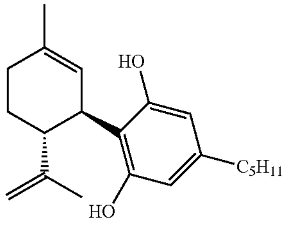

said process comprising the following steps:

a) contacting a solution [solution (S1)] of (+)-p-mentha-diene-3-ol of formula (4)

(4)

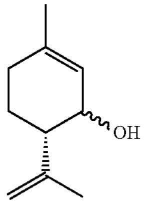

or an ester thereof and olivetol of formula (3):

(3)

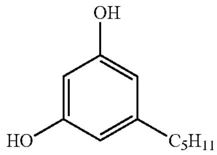

and a solution [solution (S2)] of a non-supported Lewis acid in an organic solvent, wherein said non-supported Lewis acid is $BF_3$-$Et_2O$, in a continuous flow reactor to obtain a first mixture [mixture (M1)] comprising Cannabidiol; and b) contacting mixture (M1) with a basic solution [solution (S3)] to obtain a second mixture [mixture (M2)]

c) separating Cannabidiol from mixture (M2), wherein residence time in the continuous flow reactor of step a) is between 1 to 10 minutes and wherein Cannabidiol is obtained with a molar yield of 34% and no formation of tetrahydrocannabinol.

2. The process according to claim 1 wherein the ester of (+)-p-mentha-diene-3-ol of formula (4) is an ester with a straight or branched carboxylic acid having from 1 to 5 carbon atoms.

3. The process according to claim 2 wherein the ester is the acetic ester of formula (7):

(7)

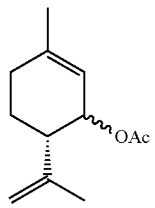

4. The process according to claim 1 wherein the Lewis acid is $BF_3$.

5. The process according to claim 1 wherein solutions (S1) and (S2) comprise dichloromethane as solvent.

6. The process according to claim 1 wherein the molar ratio between (+)-p-mentha-diene-3-ol of formula (4) or ester thereof and olivetol of formula (3) ranges from 1:1 to 1:2.

7. The process according to claim 1 wherein the basic solution (S3) is an alkali metal carbonate or bicarbonate aqueous solution.

8. The process according to claim 7 wherein the basic solution (S3) is a sodium or potassium bicarbonate solution.

9. The process according to claim 8 wherein the basic solution (S3) is a sodium bicarbonate solution.

10. The process according to claim 1 wherein step b) is accomplished by quenching mixture (M1) in solution (S3) contained in a vessel.

11. The process according to claim 1 wherein step b) is accomplished by conveying mixture (M1) to another continuous flow reactor along with solution (S3).

12. The process according to claim 1, wherein the continuous flow reactor is a microreactor.

* * * * *